(12) United States Patent
Hansen

(10) Patent No.: US 9,579,237 B2
(45) Date of Patent: Feb. 28, 2017

(54) POSTOPERATIVE COMPRESSION BINDER

(71) Applicant: Doris Hjorth Hansen, Chiaverano (IT)

(72) Inventor: Doris Hjorth Hansen, Chiaverano (IT)

(73) Assignee: QUALITEAM S.R.L., Chiaverano (IT)

( * ) Notice: Subject to any disclaimer, the term of this patent is extended or adjusted under 35 U.S.C. 154(b) by 189 days.

(21) Appl. No.: 14/495,101

(22) Filed: Sep. 24, 2014

(65) Prior Publication Data
US 2015/0094638 A1    Apr. 2, 2015

(30) Foreign Application Priority Data

Oct. 2, 2013  (EP) .................................. 13425134

(51) Int. Cl.
| | | |
|---|---|---|
| A61F 13/00 | (2006.01) | |
| A61F 13/14 | (2006.01) | |
| D05B 1/02 | (2006.01) | |
| A61F 5/03 | (2006.01) | |
| A61F 13/08 | (2006.01) | |

(52) U.S. Cl.
CPC ............. *A61F 13/148* (2013.01); *A61F 5/03* (2013.01); *A61F 13/00987* (2013.01); *A61F 13/00995* (2013.01); *A61F 13/08* (2013.01); *A61F 13/085* (2013.01); *D05B 1/02* (2013.01)

(58) Field of Classification Search
CPC ............ A61F 13/00; A61F 2013/00174; A61F 2013/00106; A61F 13/0203; A61F 2013/00468; A41F 11/16; A41F 9/002; A41F 9/02; A41D 1/20
See application file for complete search history.

(56) References Cited

U.S. PATENT DOCUMENTS

| | | |
|---|---|---|
| 693,115 A | 2/1902 | Cozzens |
| 3,194,234 A | 7/1965 | Duckman et al. |
| D349,767 S | 8/1994 | Courtet |
| 6,309,369 B1 | 10/2001 | Lebovic |
| 6,516,804 B1 | 2/2003 | Hoffman |
| D499,806 S | 12/2004 | Machin et al. |
| 6,921,375 B2 | 7/2005 | Kihara |

(Continued)

FOREIGN PATENT DOCUMENTS

WO    WO 2010/025186 A1    3/2010

OTHER PUBLICATIONS

Feb. 3, 2014 European Search Report for EP Application No. 13425134.7 (6 pages).

(Continued)

*Primary Examiner* — Ophelia A Hawthorne
(74) *Attorney, Agent, or Firm* — Popovich, Wiles & O'Connell, P.A.

(57) ABSTRACT

The present invention provides for an advanced postoperative compression binder including at least two overlapping stretchable bands. The bands are connected by stitches located within an overlapping portion of the bands. The stitches are spaced from first and seconds ends of the bands to allow individual compression-adjustments of the binder to allow compression to be adapted to the type of surgery or trauma performed and to a level of comfort desired by the patient. The invention provides for wound inspection and care without the need to open the total compression binder, which will maintain a degree of support during wound inspection and care, decrease pain and increase comfort for the patient.

14 Claims, 4 Drawing Sheets

(56) References Cited

U.S. PATENT DOCUMENTS

| | | | |
|---|---|---|---|
| D517,215 S | 3/2006 | Cheney | |
| 7,160,262 B2 | 1/2007 | Wicks | |
| 7,347,695 B2 | 3/2008 | Ware et al. | |
| D595,859 S | 7/2009 | Young | |
| D628,300 S | 11/2010 | Caden | |
| D657,063 S | 4/2012 | Chiang | |
| D658,350 S | 5/2012 | Goodman | |
| D661,402 S | 6/2012 | Chen et al. | |
| 2006/0135898 A1 | 6/2006 | Richardson | |
| 2007/0179421 A1* | 8/2007 | Farrow | A61H 9/005 602/75 |
| 2008/0251087 A1 | 10/2008 | Richardson | |
| 2010/0049109 A1 | 2/2010 | Stewart, III | |
| 2011/0004970 A1 | 1/2011 | Okamoto | |
| 2011/0112453 A1 | 5/2011 | Petiot et al. | |

OTHER PUBLICATIONS

QualiBelly Advanced brochure 2011 (2 pages).
QualiBelly brochure 2010 (2 pages).
Cheifetz et al., The Effect of Abdominal Support on Functional Outcomes in Patients Following Major Abdominal Surgery. Physiotherapy Canada, vol. 62, No. 3. pp. 242-253.

* cited by examiner

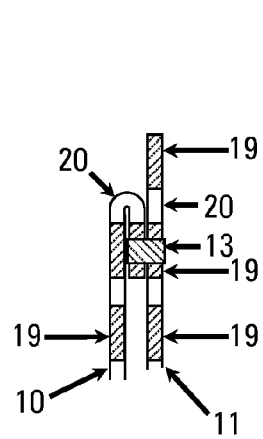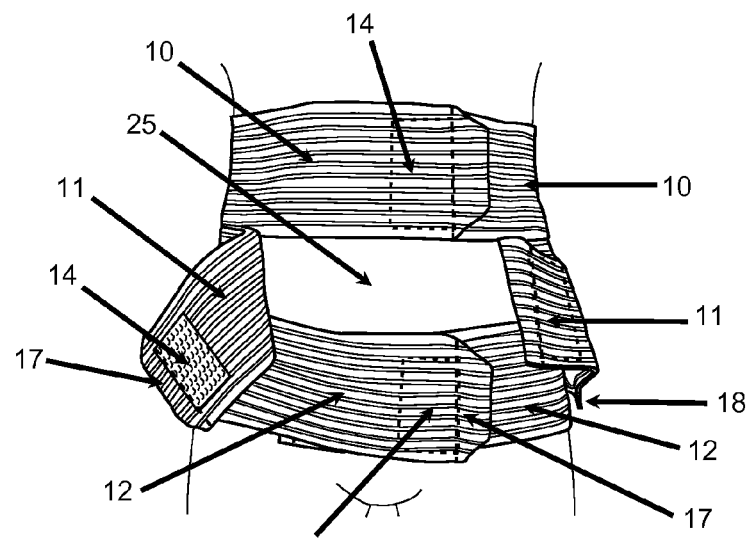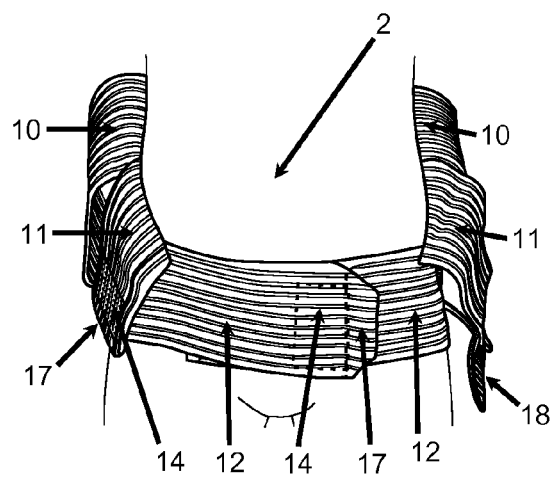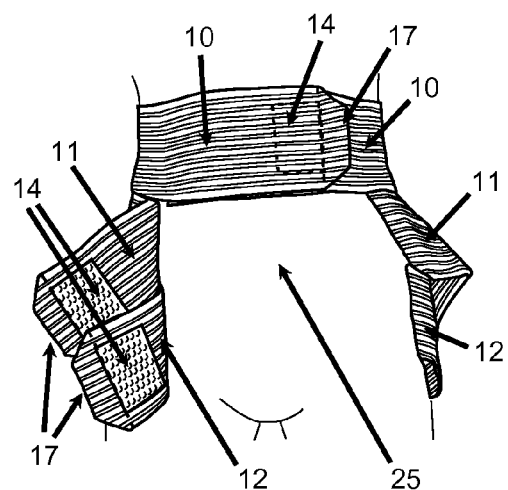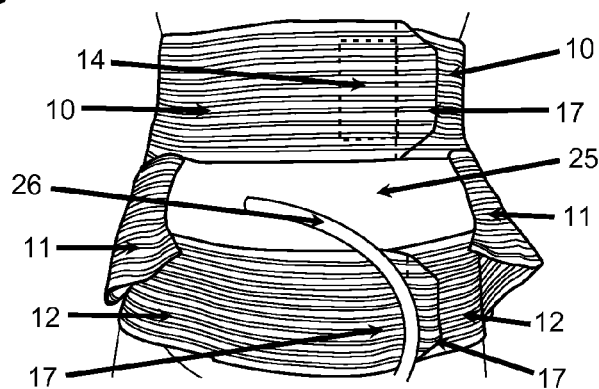
Fig. 10
Fig. 11
Fig. 12
Fig. 13
Fig. 14

POSTOPERATIVE COMPRESSION BINDER

FIELD OF INVENTION

The present invention relates to binders used for support and compression after surgical interventions or trauma to parts of the human body. In particular, the invention relates to a compression binder for use after major surgeries in the abdominal region, including, but not limited to, surgeries in the internal organs e.g. liver, pancreas, stomach, kidneys, small and large intestines, bladder and uterus, and for bariatric and other surgeries that require access through the abdominal wall. More in particular the invention relates to a compression binder made of breathable and color-stimulating material which has individual compression-adjustments at several vertical sections of the binder to comply with the type of trauma or surgery performed, and to the comfort level for compression of the patient. More in particular the invention relates to a compression binder that maintains support during wound inspection and care and allows for such wound inspection and care without it being necessary to open the total compression binder. More in particular the invention relates to a compression binder that can be transformed into a lower compression binder to relieve pressure on the upper abdominal area when patients sit down and to increase back support. More in particular the invention relates to a compression binder which can accommodate drainage tubes, ostomy devices, driver lines from Left Ventricular Assist Devices (LVAD's) or other apparatus that may exit through the abdominal wall, without the need to separate said devices from their counterparts on the external side of the abdomen, and without the need to cut holes in the material of the compression binder. More in particular the invention relates to a compression binder which has accessories to organize and fixate drainage lines and collection bottles of all sizes, driver lines for VLAD's and other items that need to be secured at a fixed position with respect to the external side of the compression binder.

BACKGROUND OF THE INVENTION

Abdominal muscles are crucial for most activities human beings do: they assist with respiration; they control the expulsive effort of coughing, sneezing, urination and defecation and assist with childbirth; they cooperate with the back muscles to flex and extend the trunk at the hips and to rotate the trunk at the waist; and they protect the internal organs by becoming rigid.

Major surgeries in the abdominal region necessitates incisions through the abdominal wall and muscles. The loss of the abdominal muscular integrity after such surgical interventions causes considerable pain and soreness in the postoperative period during respiration, coughing, movements and during all daily day activities as listed above. Such pain and soreness will continue until the abdominal muscles have healed and fully recovered their strength. Furthermore the intra-abdominal pressure (IAP) increases dramatically during coughs, sneezes, vomits, defecation, movements during exercises and when lifting anything heavy which exerts a sudden increase in stress on a wound with increased risk for dehiscence. Therefore, as well known in the art, abdominal muscles must be supported from the outside by a compression binder to prevent wound dehiscence and related wound infections, to lessen pain, to give the muscular tissue peace to heal and to increase comfort for patients and speed up recovery. Various types of interventions may in addition cause some degree of swelling and bruising after surgery. Abdominal compression will help diminish such swelling and promote the healing process and thereby decrease the time of recovery and related health care costs.

Compression binders are common and a large selection of commodity binders are available. Typically the binders consist of a wide band made of a variety of elastic or non-elastic materials, or a combination thereof, and they wrap around the patient's abdominal region and are usually closed by means of one common fabric hook and loop closure or a series of hook and eye closures. The materials used are often heavy and non-ventilated and usually created in white or beige colors. Such binders can be warm, uncomfortable to wear for a patient, and usually have the problem that they crawl up, roll or robe on the body making them further uncomfortable. Therefore, to avoid such problems a compression binder should be made of a ventilated, light, comfortable material, that does not curl up, crawl or robe on the body, and, as an additional feature, the material should be made of colors that has a stimulating psychological effect on the patient in the typical "sterile-colored" hospital environment.

The position and size of a wound depends on the type of intervention, as for example an abdominal wound after major abdominal surgery or other interventions requiring access through the abdominal wall. Accordingly the need for compression and support to the wound and abdomen will be different across the vertical width of a patients abdomen and will vary from patient to patient, and it will not be comfortable for patients to have the full abdominal region compressed, as is the state of art for most existing compression binders. Therefore it will increase comfort for a patient if the degree of compression can be adjusted at various vertical sections across the binder.

Furthermore a wound will hurt and be sensitive to manipulation, pressure, movements, temperature changes and chemicals such as wound cleaning agents. Every time a wound needs inspection and/or care, it will cause extra pain and stress for the patient. In particular such wound inspection and care is a problem for large, obese patients that have undergone surgery in the abdominal area, and for bariatric surgery patients. This is due to the gravity pull on the wound from the excess abdominal fat tissues. Such pull will not only cause pain for the obese patient, but will also increase the risk for wound infection since the wound edges will be drawn apart and the sutures may tear through the skin and cause the wound to break open. Therefore the abdominal muscles and fat tissues must be supported continuously, also during wound inspection and care, particularly for obese patients, to decrease pain and the risk for complications and infections that will lead to increased health care costs.

A compression binder that has been completely opened for inspection and care of an abdominal wound, may present a problem for large and obese patients. Not only does the excess fat tissues create a gravity pull on the wound which increases pain and risk of complications, it also makes reattachment after wound care of such binders difficult to do. Often more than one health care person is required to perform such reattachment which increases demand for availability of health care staff. Therefore, it would be desirable that reattachment of compression binders be possible without adding additional pain, stress or strain to the patient and his/her wound, and without the need to have more than one health care person present.

Postoperative pain after abdominal surgeries makes patients naturally reluctant to breathe deeply, to cough and to do their respiratory exercises since such activities increase pain and hurt due to the integral and significant part the abdominal muscles and the diaphragm take in the respiration process. It is well known in the art that inactivity increases postoperative pulmonary complications which continue to be an important risk after major abdominal surgeries. Pain and worry about straining the abdominal wound makes patients hesitate to move and get out of their hospital bed early after surgery. Such postoperative immobilization contributes to cardiovascular instability and thromboembolic complications, leading to increased health care costs. Therefore the abdominal and back muscles must be firmly supported by a compression binder to improve a patient's posture which helps patients to an improved and deeper respiration and lessened pain during their respiratory exercises and daily activities, and furthermore encourage and stimulate the patients to mobilize as early as possible.

Early mobilization after surgery is crucial for the patient's early recovery and an external compression support to the abdominal region will help the patients to walk and keep a better posture thereby improving respiration. However, a newly operated patient needs to rest often and will want to sit down with regular intervals. It is difficult and uncomfortable to sit down with a wide abdominal binder that covers the upper abdominal area, and it may cause nausea having additional pressure from such binder exerted on the stomach area in the sitting position. Therefore, a compression binder should not only help patients to achieve a better posture for improved respiration, it should also improve comfort by being able to relieve the additional pressure on the stomach when patients need to sit down for rest, which will encourage to more and earlier mobilization and less time in the hospital bed.

Major abdominal surgeries after which the patient must have one or more drainage tubes, ostomy devices or other items that exit through the abdominal wall, including driver lines from LVAD's and other apparatus, need access through wound dressings, bandages and binders that may cover the wound and abdominal area, so they can be attached to their external corresponding device and fixed to the patient or to the bed. Elastic bands and compression binders of various width that presently are used for abdominal support, can only accommodate drainage tubes and lines by separating such items from their corresponding external devices and by leading said items through existing pre-cut holes, or by cutting one or several holes in the band or binder material, before reattaching the drainage tubes, lines or other devices. Such separation and reattachment will increase the risk of infection and associated increase in health care costs. Therefore, due to the cumbersome method of accommodating such devices to existing abdominal binders, they are often not applied to the patients, if at all, until they have had drainage tubes, lines and other devices removed. Yet it has been evidenced that "when patients are provided with abdominal compression support as early as possible after surgery, it enhances early mobilization, improves patient's hospital experience by an optimized pain control and diminishes emotional stress."

Cheifetz et al., The Effect of Abdominal Support on Functional Outcomes in Patients Following Major Abdominal Surgery. Physiotherapy Canada, Volume 62, Number 3. Pg. 242-253

For these reasons drainage tubes, drainage lines, ostomy devices, driver lines and other devices must be able to exit through an abdominal compression support without the need to separate such tubes and lines from their external connection devices. Avoiding any separation and reattachment of drainage tubes and lines and other devices that may exit a patient's abdomen after surgery, will decrease the risk for complications, infections and related health care costs.

Similarly, when patients have one or more drainage tubes, stoma devices or other items that exit through the abdominal wall after major abdominal surgeries, including driver lines from LVAD's and other apparatus, abdominal binders are often not applied to the patients, if at all, since such application represents a further practical challenge to staff that have no easy method to organize and attach such devices and their accessories to the patient in order to liberalize him/her from the bed for mobilization. Staff may be prompted to wait mobilizing the patients until devices that can be removed days later, such as drains, have been taken out. In addition, patients often have more pain and will worry about accidental pulling on such drains or devices, which would hurt and increase the risk of complications. Therefore drainage tubes, lines, collection bottles, driver lines and other devices must be organized and fixated to the patient in an easy, secure and quick manner for staff so patients can get mobilized as early as possible postoperatively with less worry and less pain.

Accordingly, there is a need for an advanced compression support that provides features to decrease pain, to improve patient comfort, spirit and feeling of security, to stimulate a better posture, respiration and early mobilization, to decrease the risk of complications, infections and related health care costs, and to increase functional convenience for health care staff.

There is a great need for an advanced compression binder that can address many more of the problems that todays patient population is facing after surgery and trauma, and which health care personnel needs to handle on a daily basis. None of the abdominal support devices currently in use takes an overall approach to solve such problems. Generally, such devices are directed towards just one or two of the following: 1. Ease of closure, 2. Conformity to the body contour, 3. Universal sizing, 4. Improved wound visibility with a closed binder, 5. Dressing holder and openings for passage of drains, 6. Improve drainage bulb holding.

For example, the QualiBelly abdominal support manufactured by Qualiteam s.r.l., Chiaverano, Italy, consists of two longer and one shorter elastic band with the bands being just slightly overlapped by about 0.5 cm and being held together by large, vertical stitches which extend past the edges of the bands at the locations of connection. The large vertical stitches are about 1.4 cm in length and are spaced apart about 5 cm along the lengths of the bands. The three bands each having a closure with hook and loop fasteners. The large vertical stitches may pinch the skin on the body and make the device uncomfortable to wear. Further, the large stitches can make it uncomfortable for the patient if the upper band is folded down as is advocated in the brochures describing the product. In addition, the small overlapping of the bands, the large vertical stitches that hold the bands together with large intervals between them, fail to prevent the extrusion of fat tissue between the stitches on the bands which can be a problem, particularly in obese patients. The device also represents a fitting problem for many patients due to the difference in length of the elastic bands. If the shorter band-compression fits to a patient, the two longer band-compressions might be too long and therefore too loose, and if the two longer band-compressions fit, the shorter band-compression might be too short and therefore too tight, which in both situations can make the support uncomfortable to wear and makes it difficult to individually adjust the compression per band.

In view of the foregoing, it is the general object of the invention to provide an advanced postoperative compression binder that provides features to help patients to have decreased pain and improved comfort.

It is another object of the invention to provide an advanced postoperative compression binder that encourages a patient's spirit in the postoperative period through an increased sense of security and by color stimulation.

Another object of the invention is to provide an advanced postoperative compression binder which improves a patient's posture to achieve a deeper and more effective respiration, which helps to decrease postoperative complications and related costs of healthcare.

Another object of the invention is to provide an advanced postoperative compression binder that comfortably can be used directly on the patients skin without irritation and without heat and moisture generation.

Another object of the invention is to provide a postoperative compression binder with individual compression adjustments at various vertical sections across the binder to adapt the compression to the patient's comfort level and type of surgery performed.

Another object of the invention is to provide a postoperative compression binder where support is maintained during wound inspection and care thereby diminishing pain and stress on the wound.

Another object of the invention is to provide a postoperative compression binder where one or more sections of the support can be opened for wound inspection and care thereby increasing the functional convenience for health care staff.

Another object of the invention is to provide a postoperative compression binder for all sizes of patients, including the morbidly obese, which can be opened and closed by just one health care person.

It is yet another object of the invention to provide a postoperative compression binder that can easily and comfortably transform into a lower abdominal binder to avoid pressure on the upper abdomen and to increase comfort and respiration for patients while supporting their lower back when patients sit down.

A further object of the invention is to provide a postoperative compression binder that eliminates the need to separate drainage tubes, drainage lines, ostomy devices, driver lines for LVAD's and other apparatus that may exit from the patients abdominal wall, thereby decreasing risk of infection and complications, and the related health care costs.

A still further object of the invention is to provide a postoperative compression binder that accommodates drainage tubes, drainage lines, ostomy devices, driver lines for LVAD's and other devices that may exit from the patients abdominal wall, without the need to cut the material comprising the compression binder for allowing passage of said devices.

It is yet another object of the invention to provide a postoperative compression binder with one or more accessories that allows easy accommodation, organization and attachment of any type and size of drainage tubes and lines, drainage collection bottles or other devices attached to drainage tubes, lines or other apparatus exiting from the patient's abdominal wall to the external side of the abdominal compression support.

Yet another object of the invention is to provide a postoperative compression binder with easy means to allow measurement of eventual internal fluid build-up such as bleeding and/or seroma.

Other objects and advantages will become apparent from reading of the specifications and a study of the accompanying drawings.

SUMMARY OF THE INVENTION

The present invention provides for a postoperative compression binder with advanced features for compression, wound Inspection and care, drainage, ostomy and other device accommodation, accessories for line organization and collection device support, and for stimulation of improved posture, spirit and security sense.

The compression binder consists of at least two elastic bands that overlap and are attached to each other by small, vertical stitches that integrates into the material forming the compression binder and are arranged with an equal relatively short distance between them along the length of the elastic bands. Each elastic band has fabric hook and loop fasteners at first and second ends of the bands. The vertical stitch method of conjoining the elastic bands allows for individual compression adjustments of each elastic band which allows compression to be varied along a vertical line on the patient's abdomen so compression can be adapted to the type of surgery performed and to the level of comfort desired by the patient.

The invention provides access to the compression area for wound inspection and care by opening one or two of the bands and leaving at least one or two of the bands closed. This eliminates the need to open the total compression binder, whereby pain is decreased and comfort for the patient is increased. This maintains compression support to the patient's abdomen at all times. The compression binder achieves this access by spacing the vertical stitches a desired calculated distance from the first and second ends of each of the elastic bands. This spacing results in the first and second ends of each band being unattached to the adjoining band's over a length equal to the desired calculated distance. Thus, if one of the bands is open an access area is created by moving the ends of the open band apart to expose the abdomen. The access area will have a width equal to the distance between the first vertical stitch adjacent the first end and the first vertical stitch adjacent the second end.

Furthermore the invention allows drainage tubes, drainage lines, ostomy devices, driver lines from Left Ventricular Assist (LVAD) devices, and other devices that may exit from a patients abdomen after major surgeries or trauma, to pass from the patients abdomen to the external side of the abdominal compression binder by closing the fabric hook and loop fastener on one band above such devices, and close the fabric hook and loop fastener on the adjoining band below such devices. The invention thereby effectively eliminates the need to separate drainage tubes, drainage lines, ostomy devices, driver lines from Left Ventricular Assist (LVAD) devices, and other apparatus in order to pass them from the inside to the outside of the compression support thereby decreasing the potential for complications, infections and related health care costs.

The invention furthermore eliminates any need to cut holes in the compression binder material which avoids any tear and wear of the material.

The invention provides for accessories to organize and fixate drainage lines and drainage collection bottles of all sizes, driver lines and other devices that may need to be fixed to the external side of the compression binder for a period of time in a secure manner.

The invention provides further the possibility to be transformed into a lower compression binder when the fabric hook and loop fastener on the upper elastic band is opened and the upper band is folded down over the adjoining band, after which the fabric hook and loop fastener is closed again. Thereby any pressure on the upper abdomen is relieved, and comfort and back support for patients is increased when sitting down.

The present invention is designed taking the total needs of a postoperative patient and the health care personnel in mind. The invention promotes less pain and less wound complications, improves wound access and maintains wound support during inspection and care, improves overall comfort for the patient and functional convenience for staff, and it stimulates patients to earlier mobilization in the postoperative period, which leads to earlier discharge from the hospital with related decrease in costs of care.

BRIEF DESCRIPTION OF THE DRAWINGS

FIG. 10 is a partial view similar to FIG. 4 showing the upper elastic band folded down on top of the center elastic band.

FIG. 11 is identical with FIG. 5 but with the center elastic band of the compression binder opened for inspection and/or wound care.

FIG. 12 is identical with FIG. 5 but with the upper and center elastic band of the compression binder opened for inspection and/or wound care.

FIG. 13 is identical with FIG. 5 but with the center and lower elastic band of the compression binder opened for inspection and/or wound care.

FIG. 14 shows an advanced compression binder 1 in accordance with an embodiment of the present invention which is applied on a patient's abdominal region and which has the center elastic band of the compression binder opened for inspection and/or wound care and where a drain is exiting from the abdominal wall.

DETAILED DESCRIPTION

FIGS. 1 to 14 show an advanced compression binder according to the present invention. The illustrated embodiment is an advanced abdominal compression binder, but it should be understood that the invention is also applicable to other types of compression supports, binders and belts used on other parts of the body which can be encircled and needs compression.

Figure 1:
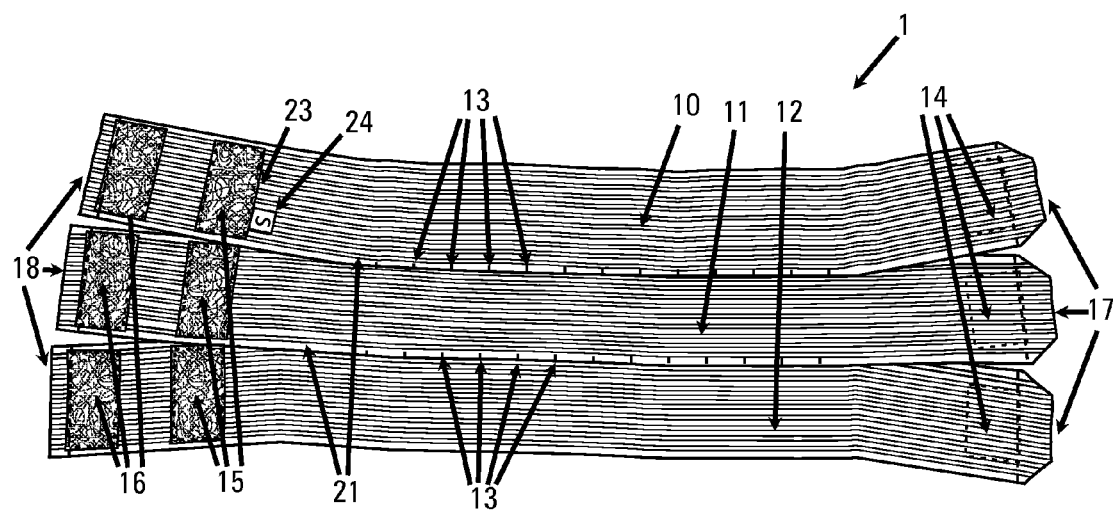
FIG. 1 is an advanced compression binder 1 in accordance with an embodiment of the present invention, which is laid out in a non-stretched fashion on a flat surface and has the outside of the compression binder facing the viewer.
Figure 4:
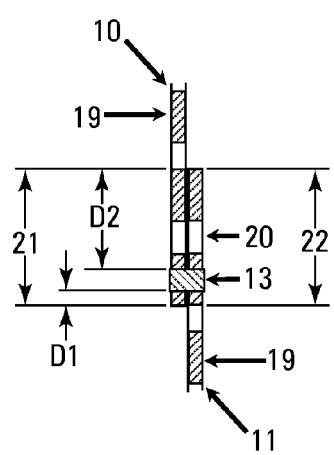
FIG. 4 shows the overlapping of two conjoining elastic bands and a vertical stitch seen in profile along line (a) in FIG. 3.

Referring now to FIG. 1 the advanced abdominal compression binder 1 is shown laid out on a flat surface with the outside of the binder facing the viewer. The outside of the binder comprises a surface opposite the patient. The inside of the binder comprises a surface adjacent or next to the patient when the binder is worn by the patient. Compression binder 1 may consist of at least two, three or more separate elastic bands 10, 11, 12, that may, as best seen in FIG. 4, overlap 21 downwards on the outside of the binder in the same direction on all the elastic bands. The band overlap may be in a range from at least 0.25 inch (0.635 cm) to 2 inches (5.08 cm). In a one embodiment the overlap 21 is 0.7 inch (1.78 cm). The elastic bands 10, 11, 12 may be attached to each other by applying a series of short vertical stitches 13 in the overlap 21 positioned so that the stitches do not extend over an edge of either of the bands being joined. The vertical stitches 13 may be positioned along the length of two conjoining elastic bands 10, 11 and 12, and may have a distance between the stitches 13 in the range of 0.5 inch (1.27 cm) to 1.8 inches (4.57 cm) in the non-stretched mode of the elastic material to create a uniform compression binder 1. In one embodiment the distance between stitches 13 is 1.4 inches (3.56 cm). The elastic bands 10, 11, 12 each have a first end 17 which may have a fabric hook fastener 14 attached adjacent to the end. Each of the elastic bands 10, 11, 12 have a second end 18 which may have two fabric loop fasteners 15, 16 attached adjacent to the end. The fabric loop fasteners 15, 16 may be spaced apart a desired distance. A sizing label 23 and a manufacturer's ID label 24 may be attached to the fabric loop fastener 15 on the elastic band 10 which may identify the elastic band 10 to be positioned as the upper band of the compression binder.

The width of each of the elastic bands 10, 11, 12 may vary according to the size of the patient. In one embodiment the compression binder 1 is available as an abdominal support with each band having a width of 4 inches or 6 inches. The length of the elastic bands 10, 11, 12 may vary according to the size of the patient. It should be noted that the use of the advanced compression binder 1 is not limited to use on a patient's abdomen, but may be used on other regions of a patient's torso, head, upper or lower extremities.

Figure 2:
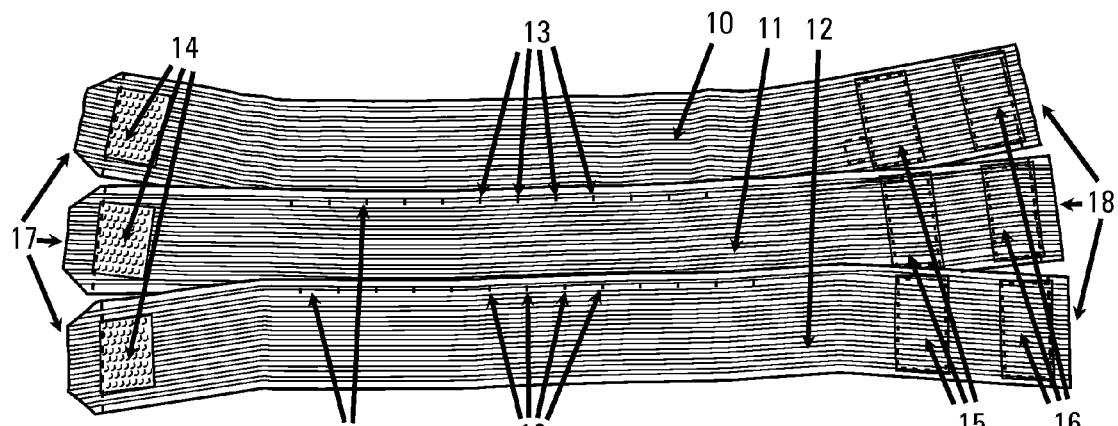
FIG. 2 is identical to FIG. 1 and shows the inside of the compression binder 1 facing the viewer.

Referring to FIG. 2 the advanced abdominal compression binder 1 of FIG. 1 is shown laid out on a flat surface with the inside surface of binder 1, the surface which is against the patient, facing the viewer. The overlap 22 of the elastic bands on the inside surface of the binder may be in the upward direction for each elastic band 10, 11, 12.

Figure 3:
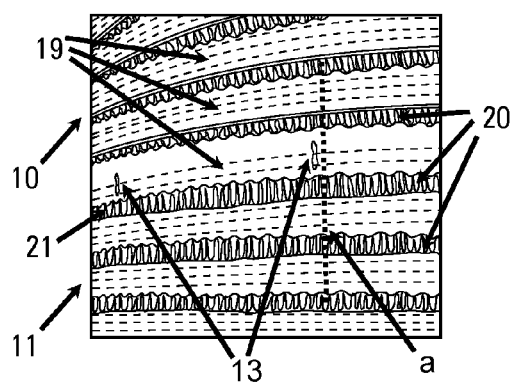
FIG. 3 shows a section of the overlapping of two elastic bands of an advanced compression binder 1 shown in FIG. 1 in accordance with an embodiment of the present invention and shows the elastic material composed of alternating dense fabric and transparent fabric, and two of the vertical stitches used to adjoin the elastic bands.

Referring now to FIG. 3, which shows a portion of bands 10 and 11 of the binder, the outside overlap 21, the vertical stitches 13 and the material in one embodiment of the invention are shown close up. Elastic bands 10, 11, 12 may be made of any suitable material that is elastic in the longitudinal direction and non-elastic in the vertical direction, that does not curl up, roll or robe on a patient's body and can receive and engage a fabric hook fastener. In one embodiment the material of elastic bands 10, 11, 12, is latex-free, consists of a mix of polyester, polyamide and elastomers and is aerated by having alternating rows of dense fabric 19 with rows of see-through ventilated fabric 20, with the edges of the elastic bands always being a row of dense fabric 19. Furthermore, the material may be colored which may stimulate the spirit and motivate patients psychologically to mobilize as early as possible in the recovery period, as for example a green color.

Referring now to FIG. 4 the outside overlap 21 and inside overlap 22 of conjoined bands 10 and 11 are shown in profile along line (a) in FIG. 3. FIG. 4 shows the dense fabric 19 alternating with ventilated fabric 20 in a one embodiment of the invention. The edge row of dense fabric 19 of one elastic band 10, 11 or 12 is positioned on the second row of dense fabric 19 of another elastic band 10, 11 or 12, which creates overlap 21 in the downwards direction on the outside and overlap 22 in the upwards direction on the inside of the binder 1. This overlap creates an overlapped portion of the binder having a width extending from a lower edge of band 10 to an upper edge of band 11. In one embodiment the vertical stitches 13 are positioned within the limits of the edge row of dense fabric 19 on the outside overlap 21 and within the limits of the second row of dense fabric 19 on the inside overlap 22. In this position the stitches 13 are located entirely within the overlapped portion and spaced a first distance D1 from the lower edge of band 10 and a second distance D2 from the upper edge of band 11. In one embodiment Distance D1 is less than distance D2. Distance D1 may be in the range of 0.04 inch (0.1 cm) to 0.12 inch (0.30 cm) and D2 may be in the range of 0.43 inch (1.1 cm) to 0.51 inch (1.3 cm). In one embodiment D1 is 0.10 inch (0.25 cm) and D2 is 0.47 inch (1.2 cm).

In one embodiment of the invention the elastic bands 10, 11, 12 may be positioned on a patient's abdominal region by encircling the patient's body and by placing a first end 17 and a second end 18 of each single elastic band on top of each other. Closure of each band may be effectuated by hook and loop fasteners 14, 15, 16 positioned on each elastic band 10, 11, 12 with at least one fabric hook material 14 at a first end 17 of each of the conjoining bands 10, 11, 12, and at least one fabric loop material 15, 16 positioned at a second end 18 of each elastic band 10, 11, 12. A fabric hook material 14 may be stitched along the width of a first end 17 of each of the elastic bands 10, 11 and 12, and the fabric loop material 15, 16 may be stitched along the width of a second end 18 of each of the elastic bands 10, 11 and 12. In one embodiment the hook and loop fastener closure potential is increased along the length of each elastic band 10, 11, 12 by stitching the fabric loop materials 15 and 16, parallel to each other and spaced apart a desired distance, for example, 2 inches.

It should be noted that the predetermined receiving fabric loop fasteners do not dictate the closure point, since the fabric hook attachments may be fastened directly on the elastic band material.

The first end 17 and second end 18 of each elastic band 10, 11 12 may have a grasping fold for comfort and to make it easier for the wearer and staff to open and close the compression binder 1. It should be noted that the closure of an abdominal compression binder 1 may be effectuated by other types of closure and is not limited to a fabric hook and loop type closure.

Figure 5:
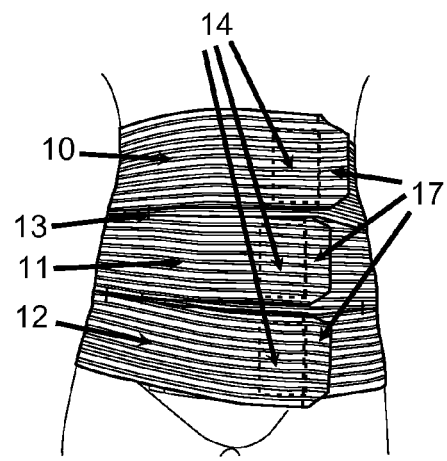
FIG. 5 is a front view of an advanced compression binder 1 in accordance with an embodiment of the present invention which is applied on the abdominal region and closed at the front left side of a patient.

Referring now to FIG. 5 an advanced abdominal compression binder 1 is shown on a patient's abdomen. Compression binder 1 is positioned on a patient's abdominal region by engaging the first end 17 of one of elastic bands 10, 11 or 12 onto the second end 18 of said elastic band, after which each of the remaining elastic bands are engaged in the same manner. The degree of compression can be adjusted individually for elastic band 10, 11 or 12 by detaching the fabric hook fastener 14 and reattaching it to fabric loop fastener 15 or 16 or directly on the material as needed until a desired degree of compression is achieved.

Figure 6:
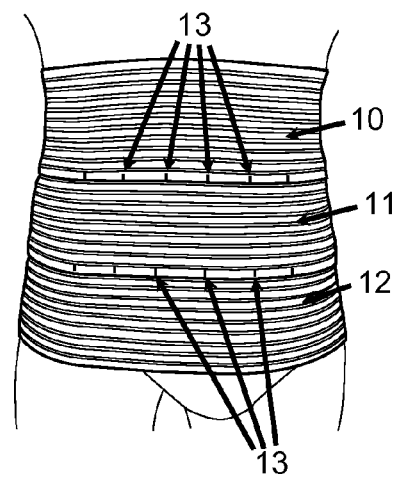
FIG. 6 is identical with FIG. 5 viewed from the back side of the patient.

FIG. 6 is a back view of the advanced abdominal compression binder 1 of FIG. 5.

Figure 7:
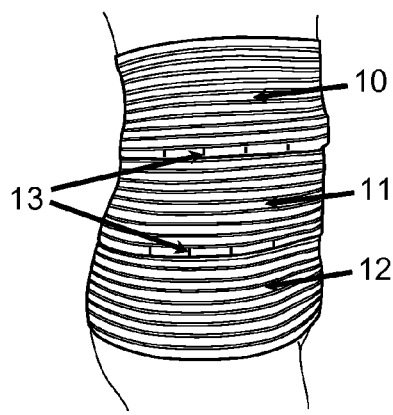
FIG. 7 is identical with FIG. 5 viewed from the right side of the patient.

FIG. 7 is a side view of the advanced abdominal compression binder 1 of FIG. 5 and illustrates how the compression binder 1 may support the posture of a patient which may, in turn, improve and encourage deeper respiration.

It should be noted that the closure position of the fabric hook and loop fastener 14, 15, 16 of the elastic bands may be anywhere along the circumferential line of the body region where it is used.

Figure 8:
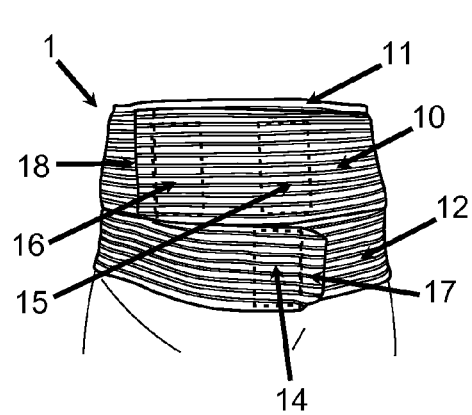
FIG. 8 shows an advanced compression binder 1 in accordance with an embodiment of the present invention which is applied on a patient's abdominal region and which has the upper elastic band of the binder folded down and re-closed on top of the center elastic band of the compression binder.
Figure 9:
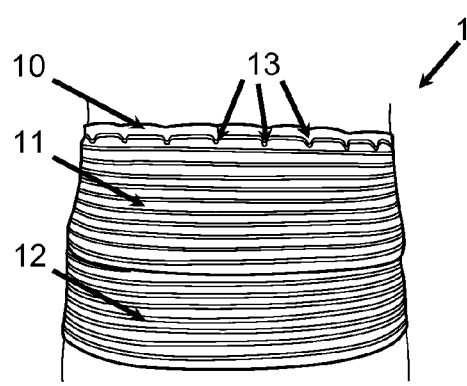
FIG. 9 is identical with FIG. 8 viewed from the back side of the patient.

Referring now to FIG. 8 and FIG. 9 and FIG. 10, an advanced abdominal compression binder 1 is shown on a patient's abdominal region. FIGS. 8 and 9 further illustrate the advanced features of compression binder 1, by showing that the upper elastic band 10 may be folded down completely on top of elastic band 11. The hook and loop fastener 14, 15 of band 10 are reattached after the band is folded down. The abdominal compression binder 1 is transformed by folding down band 10 from a 3-band to a 2-band abdominal compression support with reinforced back support in the sitting position. FIG. 9 shows the compression binder 1 seen at the back side of a patient and illustrates how the vertical stitches 13 are sized and positioned to allow the elastic band 10 to fold down parallel to elastic band 11, for improved patient comfort and reinforced back support. FIG. 10 is a profile view similar to FIG. 4 showing band 10 folded down over band 11. FIG. 10 illustrates an advantage achieved by positioning the stitches 13 entirely within the overlapping portion at a location spaced from the top edge of band 11. Specifically, FIG. 10 shows that the position of band 11 is basically unaffected and remains next to the patient when band 10 is folded down. This ensures that the binder is comfortably worn by the patient even when converted from a three band support to a two band support. Further, spacing the stitches 13 farther from the top edge of band 11 than from the bottom edge of band 10 helps ensure that band 10 aligns vertically with band 11 when folded down.

FIGS. 11 to 14 illustrate compression binder 1 on a patient's abdomen with elastic bands 10, 11 and 12 shown opened or closed in various configurations to create an open access area to the patient's abdomen. In order to ensure that the access areas are sufficiently large, stitches 13, which connect the bands, are spaced inwardly a minimum of 2 inches (5.08 cm) from the hook and loop fasteners 14 and 15. As best seen in FIG. 11 this ensures an access opening having a width W of at least 4 inches (10.16 cm).

FIG. 11 illustrates an advanced feature of the abdominal compression support 1 according to one embodiment of the invention. The center elastic band 11 is shown with the hook and loop fastener 14,15 opened, while the elastic bands 10 and 12 remain closed. This opens for a large access area to the abdominal region 25, which may have a wound that needs inspection or care, a drain, an ostomy or other device that needs inspection and care, which may take place while the patient's abdomen remains supported by elastic bands 10 and 12, and may diminish pain and discomfort during said wound inspection and care. Furthermore re-closure of elastic band 11 may easily be effectuated by a single health care person, when one or more of the other elastic bands 10, 12 may remain closed, whereby demand for additional personnel may be eliminated.

Referring to FIG. 12 the advanced abdominal compression binder 1 is shown on a patient's abdomen with the upper elastic band 10 and the center elastic band 11 shown with the hook and loop fasteners 14, 15, 16 opened, while the elastic band 12 remains closed. This results in a very large open access area to the abdominal region 25 above band 12, which may have a wound that needs inspection or care, a drain, an ostomy or other device that needs inspection and care, which may take place while the patient's abdomen may remain supported by elastic band 12 which may diminish pain and discomfort during said inspection and care. Re-closure of elastic bands 10 and 11 may easily be effectuated by a single health care person, when one or more of the elastic bands 10, 11, 12 in compression binder 1 may remain closed, whereby demand for additional personnel may be eliminated.

FIG. 13 shows, the advanced abdominal compression binder 1 on a patient's abdomen with the center elastic band 11 and the lower elastic band 12 shown with the hook and loop fasteners 14, 15, 16 opened, while the elastic band 10 may remain closed. This results in a very large open access area to the abdominal region 25 below band 10, which may have a wound that needs inspection or care, a drain, an ostomy or other device that may need inspection and care, which may take place while the patient's abdomen may remain supported by elastic band 10 which may diminish pain and discomfort during said inspection and care. Re-closure of elastic band 11 and 12 may easily be effectuated by a single health care person, when one or more of the elastic bands 10, 11, 12 in compression binder 1 may remain closed, whereby demand for additional personnel may be eliminated.

Referring to FIG. 14 the advanced abdominal compression binder 1 is shown with the hook and loop fastener 14, 15, 16 opened on the center elastic band 11, while the elastic bands 10 and 12 may remain closed as in FIG. 11. A drainage tube 26 is shown exiting from the abdomen. With the elastic bands in this configuration an open access area is created between bands 10 and 12 which allows wound inspection and care while maintaining abdominal support. Closure of elastic band 11 by reattachment of the hook and loop fasteners 14, 15 and 16 is easy and quick to perform by a single health care provider. It should be understood that drainage tube 26 is for illustrational purpose only and may be any type and size of drainage tube, driver line for LVAD's, ostomy or other device that may exit from a patients abdominal wall.

In one embodiment of the invention the vertical stitches 13 may be placed in a series along the length of the conjoining and overlapping elastic bands 10, 11, 12 with such series of vertical stitches 13 ending a desired calculated distance from the first end 17 and from the second end 18 of the elastic bands as best seen in FIG. 1 and FIG. 2. The calculated distance is at least 5 inches (12.7 cm) from the last vertical stitch in a series to the first end 17 of elastic band 10, 11, 12, and the calculated distance is at least 8 inches (20.3 cm) from the last vertical stitch in a series to the second end 18 of elastic band 10, 11, 12. The calculated distances of the vertical stitches 13 from the first end 17 and second end 18 of the bands 10, 11, 12 creates a natural opening in the horizontal and vertical directions between or adjacent the elastic bands 10 11 and 12 when one or two of the bands are in the open configuration as shown in FIGS. 11 to 14. The size of the natural openings may vary according to the calculated distance of the vertical stitches 13 from the first end 17 and second end 18 of the elastic bands 10, 11 and 12, and the natural opening may facilitate the exit of drainage tubes, ostomies, driver lines from LVAD's and other apparatus that may exit from the abdomen of a patient after surgery or trauma without separating said lines and apparatus. The elimination of the need to separate said devices may decrease the risk of infection and other complications and is achieved by closing one of the elastic bands 10, 11, 12, above said devices, as for example band 10 in FIG. 14 is shown closed above a drainage tube 26,—and close another of the elastic bands 10, 11, 12 below the said devices, as for example band 12 is shown closed below drainage tube 26 in FIG. 14.

It should be noted that the spaces between stitches 13 along the overlapping and conjoining bands 10, 11, 12 are open and may allow for passage of tubes, lines and other devices that may exit from a patient's abdomen after surgery and which may be desirable to pass from the inside to the outside of an abdominal compression support 1. Said passage between stitches 13 may be achieved after separation of said devices from their external counterparts, after which said devices may be guided through the open space between stitches 13 and reattached to their external counterparts.

The calculated distance of the vertical stitches 13 from a first and second end of the bands 10, 11, 12 in combination with the optimal spacing between vertical stitches 13 allows for individual circular compression adjustments of each of the elastic bands 10, 11 and 12, individually, around a patients abdomen or other body part. More specifically, the bands are not connected together along those portions of the bands not joined by the vertical stitches. This allows not only access to the abdominal area as shown in FIGS. 11 to 14 but also allows some degree of individual compression adjustment since one band may be compressed more or less, as desired, than an adjoining band. Individual adjustment is achieved by detaching fabric hook fastener 14 from the loop receiving fabric on one of elastic bands 10, 11, or 12 and readjusting the degree of compression of said elastic bands to accommodate the comfort level of the patient along a vertical line of the compression binder 1.

Figure 15:
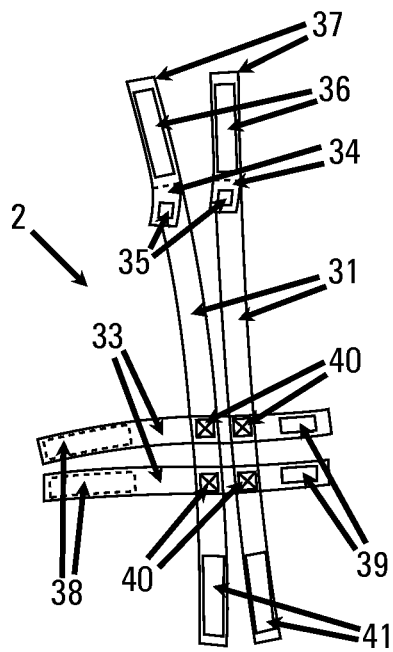
FIG. 15 is a view of the inside of a laid out universal drainage collection bottle holder accessory 2 in accordance with an embodiment of the invention.
Figure 16:
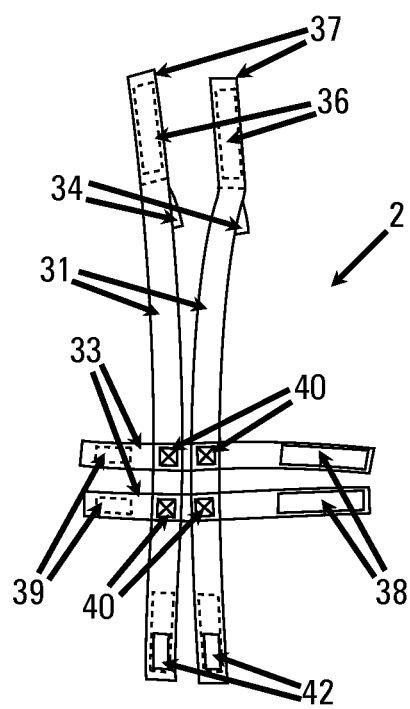
FIG. 16 is a view of the inside of a laid out universal drainage collection bottle holder accessory 2 in accordance with an embodiment of the invention.

The size, spacing and configuration of vertical stitches 13 provide additional benefits. For example, the short vertical length of the stitch combined with the stitch position within the overlap of the bands without crossing over the edge of either conjoined band allows the stitch to be integrated into the material of the binder so that the stitches do not irritate or harm the skin of the patient. Further, by maintaining a minimum band overlap as specified herein and by maintaining a maximum spacing between vertical stitches as specified herein the problem of fat tissue bulging through the binder between the stitches joining the bands is virtually eliminated. FIGS. 15 and 16, show a universal drainage collection bottle holder 2, which may be used as an accessory to the advanced abdominal compression binder 1 described herein. The drainage collection bottle holder is shown laid out flat with the inside out in FIG. 15 and laid out flat with the outside out in FIG. 16. The universal drainage collection bottle holder 2 may consist of two parallel, elastic strips 31 having a length of at least 30 inches (76.2 cm), a width of at least 1 inch (2.54 cm) and with a distance between them of at least 0.5 inch (1.27 cm). The two strips 31 may be attached to each other by crossing two shorter parallel, elastic strips 33 with a length of at least 13 inches (33 cm), a width of at least 1 inch (2.54 cm) and a distance between them of at least 0.5 inch (1.27 cm), transversally at the lower ⅓ part of the strips 31, and stitched together with a stitch pattern 30. The material of bands 31 and 33 may be any suitable material that is elastic in one direction and non-elastic in the other direction and that can receive and engage a fabric hook fastener. In a preferred embodiment the material is latex-free, aerated and consists of a mix of polyester, polyamide and elastomers. Each of strips 31 and of strips 33 may be equipped with fabric hook and loop fasteners at a first and second end to facilitate closure around objects of various sizes that may be placed on the crossing between strips 31 and 33 with the 4 stitch patterns 40.

In one embodiment strips 31 each have a fabric hook fastener 41 of a size 4 inches by 1 inch (10.16 cm×2.54 cm) stitched on the lower inside first end of the strips 31, and a fabric hook fastener 42 of a size 1.5 inches by 0.5 inch (3.81 cm×1.27 cm) stitched on the lower outside first end of the strips 31 as shown in FIG. 16. In one embodiment the upper second ends of strips 31 as shown in FIG. 15 each have a fabric loop fastener 36 of a size 4 inches by 1 inch (10.16 cm×2.54 cm) stitched to the inside of strips 31, and two short elastic strips 34 each stitched to the strips 31 at the central end of the fabric loop fastener 36, with each strip 34 having a fabric hook fastener 35 of size 0.5 inch by 0.5 inch (1.27 cm×1.27 cm) stitched onto them. In one embodiment the transversal strips 33 each have a fabric loop fastener 38 of a size 4 inches by 1 inch (10.16 cm×2.54 cm) stitched to the outside of a first end of each strip 33 as shown in FIG. 16, and a fabric hook fastener 39 of a size 1.5 inches by 0.5 inch (3.81 cm×1.27 cm) at a second end of each strip 33. It should be noted that the arrangements of fabric hook and loop fasteners may be arranged in various sizes and positions on the parallel elastic strips 31 and 33, and that the transversal attachment points with stitch patterns 40 may be positioned at any point along the length of elastic strips 31 and 33.

Figure 17:
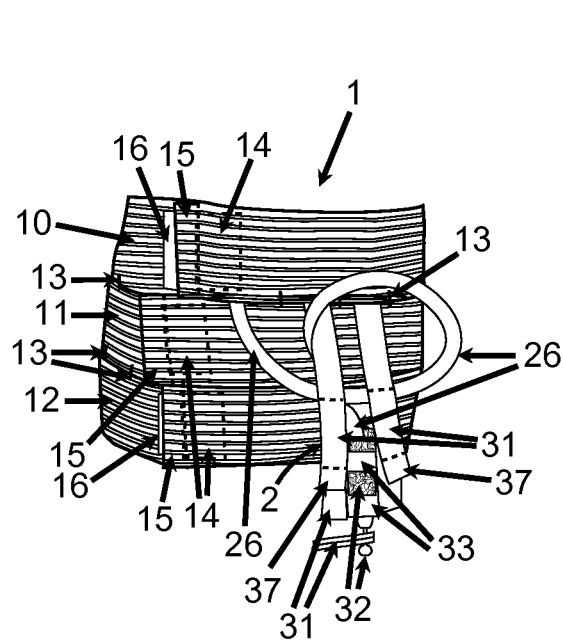
FIG. 17 shows a patient with an abdominal drainage tube wearing an advanced abdominal compression support 1 in accordance with an embodiment of the invention where the drainage tube in connected to a drainage collection bottle resting in a universal holder accessory 2 attached to the abdominal compression support.
Figure 18:
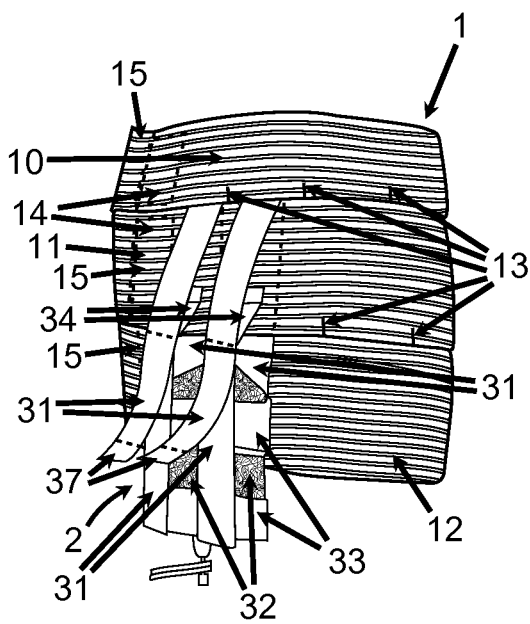
FIG. 18 shows an advanced abdominal compression support 1 in accordance with an embodiment of the invention showing the universal holder accessory 2 with a drainage collection bottle attached to the abdominal compression support 1.

Now referring to FIG. 17 and FIG. 18 an advanced abdominal compression binder 1 is shown with the universal drainage collection bottle holder 2, attached. The universal drainage collection bottle holder 2 may have the two parallel transversal elastic strips 33 closed around a drainage collection bottle 32 with fabric hook 39 and fabric loop 38 fasteners. Drainage collection bottle 32 may be of any size generally used for wound drainage collection. A universal drainage collection bottle holder 2 may have the two parallel, elastic strips 31 inserted between elastic band 11 and 12 of the abdominal compression support 1 between two vertical stitches 13, and the two parallel, elastic strips 31 may exit between two vertical stitches 13 of elastic bands 10 and 11, after which the fabric loop fastener 36 of the two elastic strips 31 each may be attached to the fabric hook fastener 42, and the fabric hook fastener 41 may be engaged against the elastic strips 33 and the fabric loop 38 material.

As can be seen in FIG. 17 a drainage tube 26 exits from a patient's abdomen between elastic band 10 and 11 at the position of the fabric hook and loop fastener on said bands, and is attached to a drainage collection bottle 32. Drainage tube 26 has been organized without separating it from its collection bottle by passing it under the two parallel elastic strips 31 by temporarily detaching the first end of strips 31 from the second end of strips 31. Drainage tube 26 is enclosed by the short elastic strips 34 of each strip 31. The short elastic strips 34 may be closed onto said strips 31 by engaging the fabric hook fastener 35 onto the fabric loop fastener 36. It should be noted that the short elastic strips 34 may be positioned on the outside of bands 31, and that short elastic strips 34 may be positioned both on the inside and outside of bands 31.

Various modifications and alterations to this invention will become apparent to those skilled in the art without departing from the scope and spirit of this invention. It should be understood that this invention is not intended to be unduly limited to by the illustrative embodiments and examples set forth herein and that such examples and embodiments are presented by way of example only with the scope of the invention intended to be limited only by the claims set forth herein as follows.

What is claimed is:

1. A compression binder for supporting a portion of a patient's body comprising:
 at least two stretchable bands including upper and lower bands, each band having a length and having first and second ends, the first and second ends each having a fastener, the fastener on the first end being adjustably connectable to the fastener on the second end to vary a tension applied to the patient's body, each band further having a width defined by upper and lower edges extending between the first and second ends, each band having an inner surface configured to be positioned next to the patient and an outer surface configured to be positioned away from the patient; and
 a plurality of vertical stitches connecting the upper and lower bands, the inner surface of the upper band overlapping the outer surface of the lower band to form an overlapping portion having a width between the lower edge of the upper band and the upper edge of the lower band in a range of 0.25 inch to 2 inches, the vertical stitches being located entirely within the overlapped portion at positions spaced a first distance D1 above the lower edge of the upper band and a second distance D2 below the upper edge of the lower band, the vertical stitches being spaced apart a distance in a range of 0.5 inch to 1.8 inches.

2. The compression binder of claim 1 wherein D1 is less than D2.

3. The compression binder of claim 2 wherein D1 is 0.125 inch and D2 is 0.375 inch.

4. The compression binder of claim 1 wherein the vertical stitches are spaced from the first end by a distance equal to at least 5 inches.

5. The compression binder of claim 4 wherein the vertical stitches are spaced from the second end by a distance equal to at least 8 inches.

6. The compression binder of claim 1 wherein the width of the overlapping portion comprises 0.7 inch.

7. The compression binder of claim 1 wherein the vertical stitches are spaced apart a distance of 1.4 inches.

8. A method of making a compression binder for supporting a portion of a patient's body, the compression binder having at least two stretchable bands including upper and lower bands, each band having a length and having first and second ends, the first and second ends each having a fastener, the fastener on the first end being adjustably connectable to the fastener on the second end to vary a tension applied to the patient's body, each band further having a width defined by upper and lower edges extending between the first and second ends, each band having an inner surface configured to be positioned next to the patient and an outer surface configured to be positioned away from the patient, the method comprising:

connecting the upper and lower bands with a plurality of vertical stitches such that the inner surface of the upper band overlaps the outer surface of the lower band to form an overlapping portion having a width between the lower edge of the upper band and the upper edge of the lower band in a range of 0.25 inch to 2 inches, the vertical stitches being located entirely within the overlapping portion at positions spaced a first distance D1 above the lower edge of the upper band and a second distance D2 below the upper edge of the lower band, the vertical stitches being spaced apart a distance in a range of 0.5 inch to 1.8 inches.

9. The method of claim 8 wherein D1 is less than D2.

10. The method of claim 9 wherein D1 is 0.125 inch and D2 is 0.375 inch.

11. The method of claim 8 wherein the vertical stitches are spaced from the first end by a distance equal to at least 5 inches.

12. The method of claim 11 wherein the vertical stitches are spaced from the second end by a distance equal to at least 8 inches.

13. The method of claim 8 wherein the width of the overlapping portion comprises 0.7 inch.

14. The method of claim 8 wherein the vertical stitches are spaced apart a distance of 1.4 inches.

* * * * *